US010362986B2

(12) United States Patent
Heneghan et al.

(10) Patent No.: US 10,362,986 B2
(45) Date of Patent: Jul. 30, 2019

(54) SLEEP MONITORING SYSTEM

(71) Applicant: University College Dublin, National University of Ireland, Dublin, Dublin (IE)

(72) Inventors: Conor Heneghan, San Diego, CA (US); Stephen Redmond, Dublin (IE)

(73) Assignee: University College Dublin, National University Of Ireland (IE)

( * ) Notice: Subject to any disclaimer, the term of this patent is extended or adjusted under 35 U.S.C. 154(b) by 312 days.

(21) Appl. No.: 14/297,271

(22) Filed: Jun. 5, 2014

(65) Prior Publication Data
US 2014/0358014 A1 Dec. 4, 2014

Related U.S. Application Data

(62) Division of application No. 11/718,301, filed as application No. PCT/IE2005/000122 on Nov. 2, 2005, now Pat. No. 8,784,324.

(30) Foreign Application Priority Data

Nov. 2, 2004 (IE) .................................... 2004/0731

(51) Int. Cl.
*A61B 5/00* (2006.01)
*A61B 5/024* (2006.01)
(Continued)

(52) U.S. Cl.
CPC ........ *A61B 5/4806* (2013.01); *A61B 5/02405* (2013.01); *A61B 5/113* (2013.01);
(Continued)

(58) Field of Classification Search
None
See application file for complete search history.

(56) References Cited

U.S. PATENT DOCUMENTS 5,105,354 A 4/1992 Nishimura
5,187,657 A 2/1993 Forbes
(Continued)

FOREIGN PATENT DOCUMENTS

EP 0450341 A2 10/1991
WO 03099114 A1 12/2003

OTHER PUBLICATIONS

Zongker et al., Algortihms for Feature Selection: An Evaluation, IEEE Procedings of ICPR 1996.*
Hodsman et al.—Data collection and analysis from a respiratory inductance plethysmograph; 1987.*
Pagani et al.—Power Spectral Analysis of Heart Rate and Arterial Pressure Variabilities as a Marker of Sympatho-Vagal Interaction in Man and Conscious Dog, 1986.*
(Continued)

*Primary Examiner* — Tiffany Weston
*Assistant Examiner* — Jay B Shah
(74) *Attorney, Agent, or Firm* — Botos Churchill IP Law LLP

(57) ABSTRACT

A sleep monitoring system includes an ECG device and a respiration inductance plethysmogram which monitor cardiac activity and physical respiration respectively and feed representative signals to a digital data processor. Operations process the beat interval data, while in a second thread, operations independently process the amplitude modulation of the ECG data caused by the respiratory motion of the subject. The inductance plethysmogram device provides an input to the processor which represents respiration as directly monitored independently of the ECG. Operations process this direct respiration data independently and in parallel, in a third thread. All extracted features are fed to a classifier which in step combines selected combinations of features to make decisions in real time.

20 Claims, 3 Drawing Sheets

(51) Int. Cl.
*A61B 5/113* (2006.01)
*G16H 50/20* (2018.01)
*G06F 19/00* (2018.01)

(52) U.S. Cl.
CPC .......... *A61B 5/4812* (2013.01); *A61B 5/7264* (2013.01); *G06F 19/00* (2013.01); *G16H 50/20* (2018.01); *A61B 5/7267* (2013.01)

(56) References Cited

U.S. PATENT DOCUMENTS

| | | | |
|---|---|---|---|
| 5,280,791 A | | 1/1994 | Lavie |
| 5,325,856 A | * | 7/1994 | Nitzsche .............. A61B 5/0464 600/516 |
| 5,902,250 A | | 5/1999 | Verrier et al. |
| 7,025,729 B2 | | 4/2006 | de Chazal et al. |
| 2002/0169384 A1 | * | 11/2002 | Kowallik .......... A61M 16/0051 600/529 |
| 2003/0055348 A1 | * | 3/2003 | Chazal ............... A61B 5/04325 600/509 |
| 2005/0209521 A1 | | 9/2005 | Kettunen et al. |
| 2006/0184056 A1 | | 8/2006 | de Chazal et al. |

OTHER PUBLICATIONS

Guilleminault et al.—Variability of respiratory effort in relation to sleep stages in normal controls and upper airway resistance syndrome patients, 2001.*
Busek et al.—Spectral Analysis of Heart Rate Variability in Sleep; Physiol. Res. 54: 369-376, 2005.*
Toscani et al.—Human heart rate variability and sleep stages; Ital. J, Neurol. Sci. 17:437-439, 1996.*
Snyder et al.—Changes in respiration, heart rate, and systolic blood pressure in human sleep; J Appl Physiol. May 1964;19:417-22.*
Calleja et al. Comparison of a cardiorespiratory device versus polysomnography for diagnosis of sleep apnoea. European Respiratory Journal 2002, vol. 20, pp. 1505-151 0.
Chazal et al. Automated Processing of the Single-Lead Electrocardiogram for the Detection of Obstructive Sleep Apnoea. Transactions on Biomedical Engineering, Jun. 2003, vol. 50, No. 6, pp. 686-696.
Weese-Mayer et al. Comparison of Apnea Identified by Respiratory Inductance Plethysmography with That Detected by Endtidal C02 or Thermistor. Date: 2000.

* cited by examiner

SLEEP MONITORING SYSTEM

CROSS-REFERENCE TO RELATED APPLICATIONS

The present application is a divisional of U.S. patent application Ser. No. 11/718,301, filed on Feb. 2, 2009, which application is a national phase entry under 35 U.S.C. § 371 of International Application No. PCT/IE2005/000122 filed Nov. 2, 2005, which claims priority from Irish Patent Application No. 2004/0731 filed Nov. 2, 2004, all of which are hereby incorporated herein by reference.

FIELD OF THE INVENTION

The invention relates to monitoring of a person's sleep pattern.

PRIOR ART DISCUSSION

It is known to provide a system to receive and process signals from sensors in order to monitor a person's sleep pattern. In one approach sleep stages are determined using signals from a polysonmogram system, in which the sleep staging component is based on measuring electroencephalograms (EEG) which are a direct measurement of brain activity. This approach has a number of disadvantages. First of all, polysonmogram monitoring equipment is complex and generally needs to be operated and analyzed in a clinic by skilled technicians. The patient is required to visit a clinic for an overnight study where skilled technicians attach the electrodes to the head, chest, chin and leg, together with a chest band and an airflow monitor. This is a costly and time-consuming process. If the polysonmogram system is operated by a patient at home, there is the requirement that the electrodes are attached correctly, and in particular that the EEG electrodes are correctly placed and attach, or otherwise the extremely low voltage EEG signals will not be recorded correctly. Furthermore, the use of a number of electrodes attached to the head during sleep is uncomfortable and disrupts the patient's sleep.

In another approach, motion based systems (actimetry) are used. However, such systems have the disadvantage that they can only distinguish between sleep and wake, with poor accuracy in patients with sleep disorders.

U.S. Pat. No. 5,280,791 describes an approach in which cardiac R-R wave intervals are used to designate sleep as REM or non-REM. A power spectrum of the cardiac R-R interval is calculated.

The prior art systems do not appear to analyse specific sleep stages sufficiently to recognise periods of wakefulness. In addition, where stages such as REM and non-REM are differentiated it appears that the performance is quite poor as the decision is based on comparison of a single parameter with a previously determined threshold value.

Therefore the current state of the art in determining sleep stages is limited by (a) the need to directly measure brain activity, and (b) poor performance when using observations of single parameters of cardiac activity.

SUMMARY OF THE INVENTION

According to the invention there is provided a sleep monitoring system comprising:
an interface for receiving sensor signals;
a processor for extracting a plurality of features from the sensor signals; and
a classifier for generating an output indicating sleep stage according to classification of the features.

In one embodiment, the processor extracts time domain and frequency domain features.

In one embodiment, the processor measures heartbeat intervals from cardiogram sensor signals and uses said measurements to extract features.

In one embodiment, the extracted features include mean interval per epoch, standard deviation of intervals, longest interval, and shortest interval.

In another embodiment, the processor measures amplitude modulation of the cardiogram sensor signals caused by respiratory motion of a person and uses said measurement to extract features.

In one embodiment, the extracted features include variance of a derived respiratory signal, and power of the respiratory signal at a frequency band.

In one embodiment, the extracted features include the dominant frequency of respiration and the power at the dominant respiratory frequency.

In one embodiment, the processor independently extracts features from the heartbeat interval measurements and from the amplitude modulation measurements.

In a further embodiment, the interface receives sensor signals from a device for physically monitoring patient respiration.

In one embodiment, the processor measures variations in signals from said device.

In one embodiment, the processor uses said measurements to independently extract features.

In one embodiment, the features extracted by the processor from the signals from said device include ribcage respiratory effort in each of a plurality of frequency bands, envelope power, and breath length variation.

In one embodiment, the interface receives sensor signals from devices simultaneously monitoring patient respiration and patient cardiograms, and the processor simultaneously processes said signals.

In one embodiment, said device comprises an inductance plethysmograph.

In one embodiment, the processor uses measurements from said sensor signals to extract features independently from extraction of features from cardiogram sensor signals.

In one embodiment, the features are extracted for each of a series of epochs.

In one embodiment, the epochs have a duration of less than 30 seconds.

In one embodiment, the processor extracts detrended features derived from a plurality of epochs in sequence.

In one embodiment, the detrended features are generated by subtracting a local mean signal from epoch feature values.

In one embodiment, the classifier operates according to a discriminant classifier model.

In one embodiment, the classifier comprises a search process for identifying a subset of the features to use for optimum classification performance.

In one embodiment, the search process performs a sequential forward floating search, in which a coefficient is a measure of an inter-rater agreement taking account of a prior probability of a specific class occurring.

In one embodiment, said process executes passes which add a feature that most improves performance to already-selected features.

In another aspect, the invention provides a sleep monitoring method performed by a system comprising a sensor interface and a processor, the method comprising the steps of:

the interface receiving signals from at least one sensor monitoring a patient while asleep;

the processor extracting a plurality of features from the sensor signals; and the processor, operating as a classifier, generating an output indicating sleep stage according to classification of the features.

DETAILED DESCRIPTION OF THE INVENTION

Brief Description of the Drawings

The invention will be more clearly understood from the following description of some embodiments thereof, given by way of example only with reference to the accompanying drawings in which.

DESCRIPTION OF THE EMBODIMENTS

Figure 1:
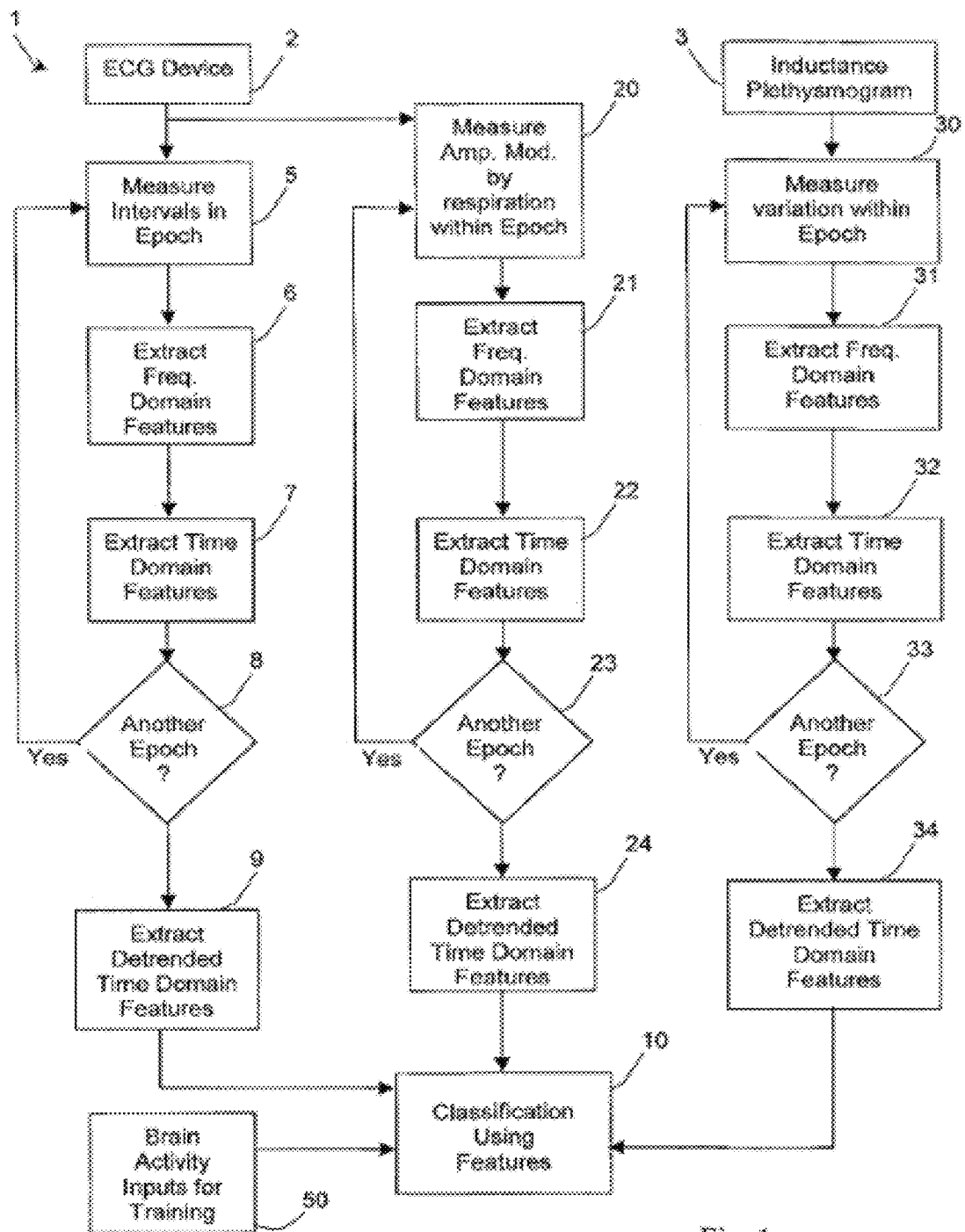
FIG. 1 is a flow diagram illustrating operation of a sleep monitoring system of the invention.

Referring to FIG. 1 a system of the invention includes an ECG device 2 and a respiration inductance plethysmogram 3 which monitor cardiac activity and physical (ribcage) respiration respectively and feed representative signals to a digital data processor. The processor is programmed to implement operations 5-10, 20-24, and 30-34 of FIG. 1 to generate an indication of the current sleep stage of a patient. Alternative devices for measurement of respiration may also be employed such as impedance pneumograms or air-flow tachometers.

Figure 2A:
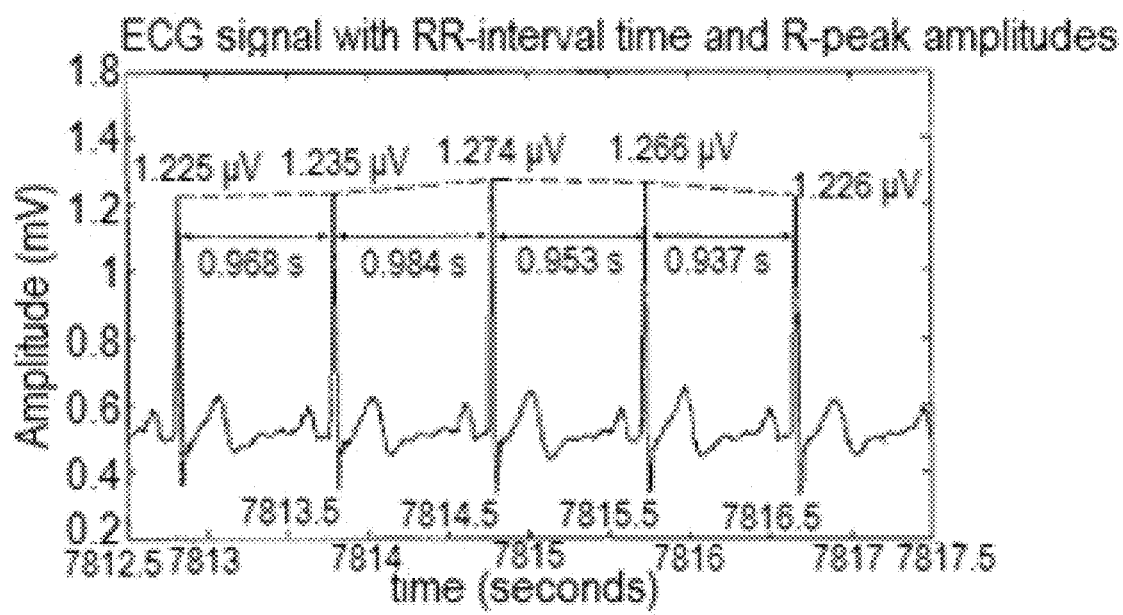
FIGS. 2A and 2B are plots of ECG and respiration inductance plethysmograph signals (sensor data) showing parameters extracted such as interbeat interval, QRS amplitude, and interbreath interval.
Figure 2B:
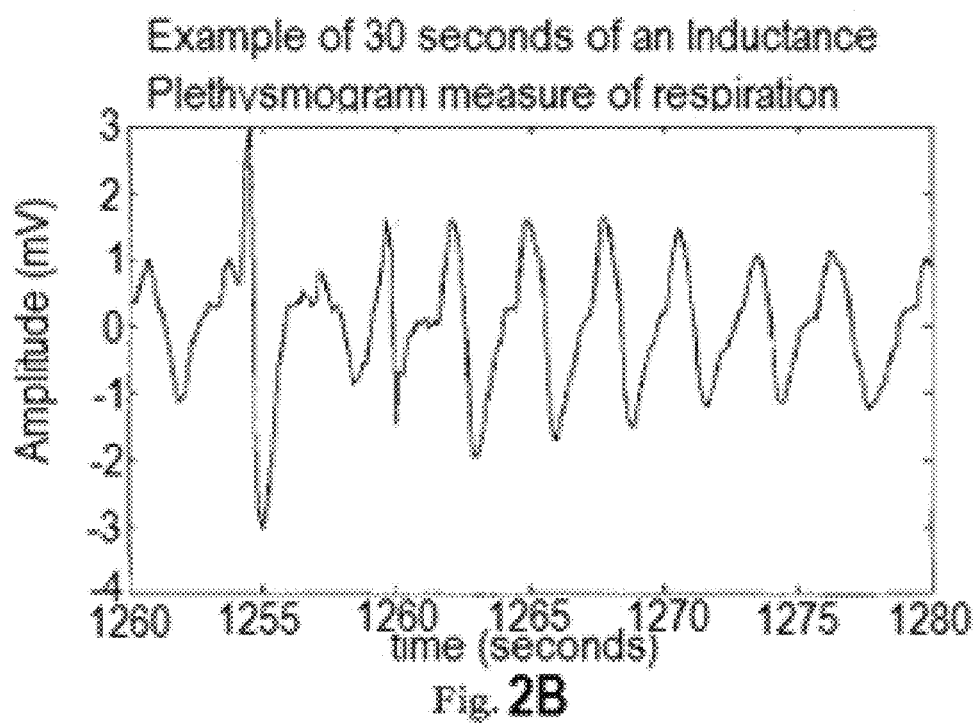
Figure 3:
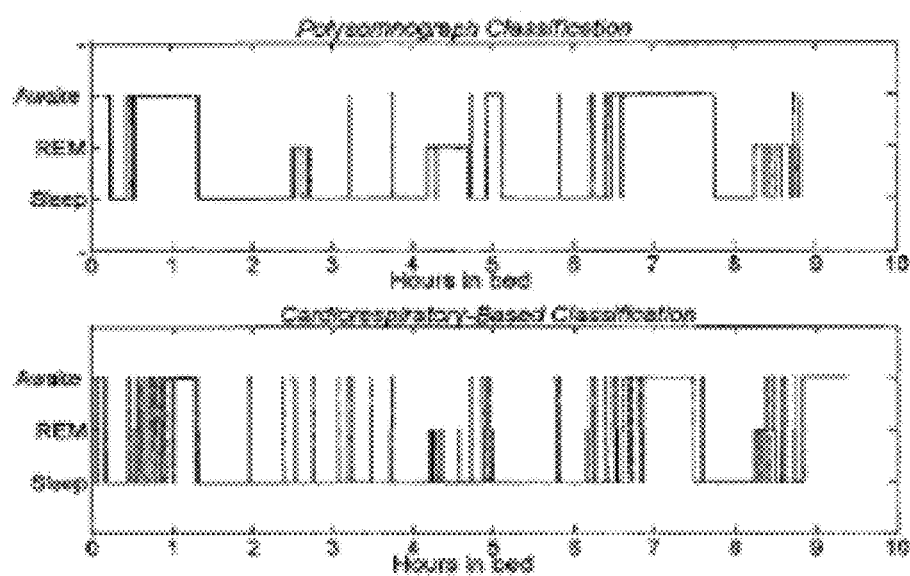
FIG. 3 is a plot of the possible outputs from the sleep staging system, in which the upper panel represents the stages of a person's sleep over one night, broken into periods of Wake, Non-REM Sleep, and Sleep.

Referring also to FIGS. 2A and 2B the electrocardiogram (ECG) device 2 provides a processor input signal containing information concerning the heart beat intervals and also respiration. The beat intervals are determined by directly measuring the time intervals between peaks in the ECG input. In the example of FIG. 2A these are 0.968 s, 0.984 s, 0.953 s, and 0.937 s.

A first set of respiration information is derived indirectly by monitoring the modulation of the amplitude of the ECG signal provided by the device 2 which is caused by the respiration pattern.

The operations 5-9 process the beat interval data, while in a second thread, the operations 20-24 independently process the amplitude modulation of the ECG data caused by the respiratory motion of the subject.

The inductance plethysmogram device 3 provides an input to the processor which represents respiration as directly monitored independently of the ECG. An example of this input is shown in FIG. 2B. The operations 30-34 process this direct respiration data independently and in parallel, in a third thread.

All three strands independently extract features. Because the operations 20-24 and 30-34 both process respiration data the features they extract should in theory be the same. However, in practice they are typically different and the system benefits from having both.

Figure 4:
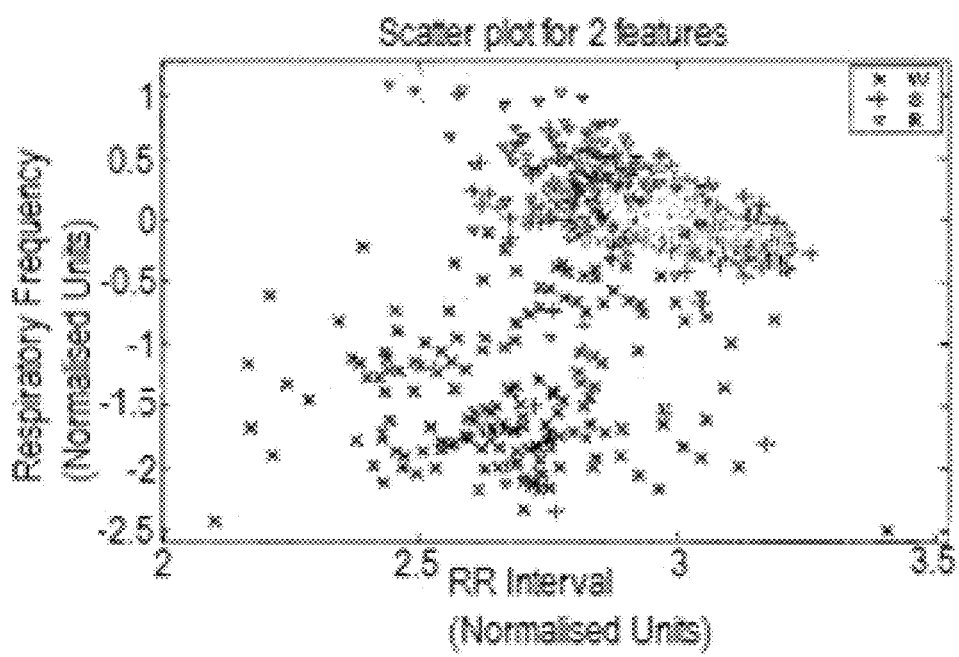
FIG. 4 is a plot illustrating how features from different sleep stages can form different clusters in the classification space.

All extracted features are fed to a classifier which in step 10 combines selected combinations of features as shown in FIG. 4 to make decisions in real time. Because many extracted features are available to the classifier it has a rich body of knowledge available to it. This provides the benefit of:

(a) very accurate and consistent determination of the current sleep stage, (b) excellent versatility because a wide range of sleep stages and sub-stages can be defined by appropriate training of the classifier, even stages with relatively little difference between them, and (c) a high level of system robustness since loss of data from one sensor (either ECG or respiration) can be compensated for by employing data from the other.

Referring again to FIG. 1, in step 5 the processor measures intervals in the ECG input for an epoch of, say, 30 seconds. In step 6, it uses this data to extract frequency domain features such as power in different bands, power at specific frequencies, and ratio of power and bands.

In step 7 it extracts time domain features such as mean interval per epoch, standard deviation of intervals, longest interval, and shortest interval. It is also advantageous to extract intrabeat interval, such as the QT or PR interval for each beat, as these are also indicative of the underlying physiological state of the subject.

As indicated by the decision step 8 these features are extracted for each of a series of epochs in a time period such as 15 mins. In step 9 the processor extracts "detrended" time domain features across all of the epochs for a time period. A "detrended" feature is one in which a new signal is formed by subtracting off the local mean signal.

For the ECG-derived respiration data the processor in step 20 measures the amplitude modulation caused by the sleep respiration. In steps 21 and 22 frequency domain and time domain features are extracted. These include the overall variance of the derived respiratory signal, the power of the respiratory signal at various frequency bands, the dominant frequency of respiration (e.g., 16 breaths per minute), and the power at the dominant respiratory frequency (which reflects the amplitude of respiration).

As shown by the decision step 23, these are repeated for each epoch in succession.

The operations 30-34 use the direct respiration signal to measure the amplitude modulation in step 30, and extract frequency domain and time domain features in steps 31 and 32. As indicated by the decision step 33 these features are extracted for each epoch in turn. Detrended features are extracted in step 34. The features for this process are the same as those for the process 20-24.

The classifier is initially trained using brain activity inputs 50 as these are the most representative of sleep stages, and provide an accurate baseline to train the classifier. Thus, the system of the invention can achieve the accuracy of a system which uses brain activity inputs without the need for the inconvenience of brain activity monitoring sensors. Moreover, the system can be readily applied to new subjects since the training across previous subjects with known sleep stages has established the correct decision parameters for the system. The classifier can also be preferentially trained to optimise performance on a single individual.

Examples

Feature Extraction

In an automated sleep staging system features are extracted from each 30 s. Sample data was collected from a database composed of overnight recordings from 37 subjects. RR-Interval Series Features: To calculate a power spectral density estimate, the data ($RR_{norm}$ intervals falling within the epoch) from the epoch is zero-meaned, windowed (using a Hanning window), and the square of its Discrete Fourier Transform (DFT) is taken as a single periodogram estimate of the interval based power spectral density. The x-ordinate of this estimate is in cycles/interval, which can be converted to cycles/second by dividing by the mean RR for the epoch. From this spectral estimate, five features are calculated:

the logarithm of the normalized LF (power in the 0.05-0.15 Hz band),
the logarithm of the normalized HF (power in the 0.15-0.5 Hz band), where normalization is achieved by dividing by the total power in the VLF, LF, and HF bands (0.01-0.5 Hz),
the LF/HF power ratio
the mean respiratory frequency, which is defined by finding the frequency of maximum power in the HF band, and
the logarithm of the power at the mean respiratory frequency.

In addition to the RR spectral features, we also used a range of temporal RR features for each 30 s epoch. These features were:

the mean $RR_{norm}$,
the standard deviation of $RR_{norm}$,
the difference between the longest and shortest $RR_{norm}$ interval in the epoch, and
the mean value of the $RR_{detrend}$ in the epoch.

The difference between longest and shortest $RR_{norm}$ within the epoch is an attempt to quantify some of the dynamic behavior within the epoch (perhaps waking epochs are more dynamic than sleep.) The mean $RR_{detrend}$ in one epoch is an attempt to examine the short-time variation in the RR interval series. Since each $RR_{detrend}$ value is a measure of the present $RR_{norm}$ relative to the previous 15 minutes of $RR_{norm}$, the mean $RR_{detrend}$ of an epoch is a measure of whether the heart rate in the present epoch is less than or greater than it has been over the last 15 minutes. This allows the discrimination of sudden rises in the heart rate, indicating short arousals, which may not rise significantly above the heart rate of other epochs of sleep.

ECG Derived Respiratory Features: The EDR epoch is taken as the EDR points corresponding to the R peaks falling within the epoch. The spectrum is calculated as for the RR interval series. From the EDR spectrum, the VLF (0.01-0.05 Hz), LF (0.05-0.15 Hz), HF (0.15-0.5 Hz) powers, respiratory frequency, and the power at respiratory frequency are estimated. The standard deviation of each epoch's EDR was also calculated.

RR-EDR Cross-Spectral Features: The VLF (0.01-0.05 Hz), LF (0.05-0.15 Hz), HF (0.15-0.5 Hz) powers were calculated from the cross-spectrum of the RR interval series and EDR for each epoch.

Ribcage Respiratory Effort Features: As with the RR interval series and the EDR, we calculate the ribcage respiratory effort spectrum as the square of the DFT of the ribcage respiratory effort signal for that epoch, windowed with a Hanning window. From the spectrum we calculate the logarithm of the power in the 3 bands—VLF (0.01-0.05 Hz), LF (0.05-0.15 Hz) and HF (0.15-0.5 Hz). The definition of these bands is taken directly from the corresponding definitions for ECG signals. Furthermore we estimate the respiratory frequency as the frequency of peak power in the range of 0.05 Hz-0.5 Hz, and also the logarithm of the power at that frequency. In the following table features 1-9 are derived from the ECG, and include both time and frequency domain heart beat features. The features 10-15 are also derived from the ECG signals, however, in this case they are derived from the amplitude modulation of the ECG caused by the respiration. The features 16-18 are derived from the preceding features. It should be noted that the steps of FIG. 1 are not necessarily carried out in the order indicated. The time domain features may be extracted before the frequency domain features or in parallel. Also, as shown below for the features 16-18 any of the steps 6, 7, 21 22, 31, or 32 may include additional feature extraction based on previously-extracted features. Finally, the features 19-27 of Table I below are extracted in steps 31 and 32.

TABLE I

FEATURE LIST

| | | |
|---|---|---|
| 1 | RR LF band (frequency domain) | RR Interval based features |
| 2 | RR HF band (frequency domain) | |
| 3 | RR standard deviation (time domain) | |
| 4 | RR respiratory freq (frequency domain) | |
| 5 | RR respiratory power (frequency domain) | |
| 6 | LF/HF Ratio (frequency domain) | |
| 7 | Longest Shortest RR difference (time domain) | |
| 8 | Detrended RR mean (time domain) | |
| 9 | RR mean (time domain) | |
| 10 | EDR VLF band (frequency domain) | EDR based features |
| 11 | EDR LF band (frequency domain) | |
| 12 | EDR HF band (frequency domain) | |
| 13 | EDR standard deviation (time domain) | |
| 14 | EDR respiratory frequency (frequency domain) | |
| 15 | EDR respiratory power (frequency domain) | |
| 16 | RR-EDR Cross spectrum VLF band (freq. dom.) | EDR-RR Interval based features |
| 17 | RR-EDR Cross spectrum LF band (freq. dom.) | |
| 18 | RR-EDR Cross spectrum HF band (freq. dom.) | |
| 19 | Ribcage Respiratory effort VLF band (freq. dom.) | Ribcage effort based features |
| 20 | Ribcage Respiratory effort LF band (freq. dom.) | |
| 21 | Ribcage Respiratory effort HF band (freq. dom.) | |
| 22 | Ribcage Respiratory effort respiratory frequency (freq. dom.) | |
| 23 | Ribcage Respiratory effort respiratory power (freq. dom.) | |
| 24 | Envelope Power (time domain) | |
| 25 | Breath by breath correlation (time domain) | |
| 26 | Breath length variation (time domain) | |
| 27 | Time domain respiratory frequency (time domain) | |

As set out above we derive several time domain features from the ribcage respiratory effort signal. The first is an estimate of its envelope power. We find the standard deviation of the peak values for the epoch, and similarly the standard deviation of the troughs. We then find the mean of the two values and divide by the standard deviation of the ribcage respiratory effort signal for the epoch. Essentially we are measuring the average top and bottom envelope powers as a fraction of the total signal power for the epoch. We denote this feature "Envelope Power". The second time domain feature attempts to measure a breath-by-breath correlation. We define a breath cycle as the time from the trough of one breath to the trough of the next. We find the cross-correlation of the adjacent breaths. Clearly, in most cases the breaths will be of different lengths, in this case the shorter is padded with zeros to make it of equal length. We find the maximum cross-correlation value and divide it by the maximum of the energy of either breath alone to normalize the maximum cross-correlation value. The maximum cross-correlation values, for all pairs of adjacent breaths in the epoch, are then averaged. We denote this feature "Breath-by-Breath Correlation". The third time domain feature is a further measure of breath-by-breath variation. We take the standard deviation of the time between peak locations, similarly we take the standard deviation of the time between trough locations. We then take the mean of these two deviations. We denote this "Breath Length Variation". Finally we derive a second estimate of the respiratory frequency, using non-spectral means. We calculate the mean time between adjacent peaks and between adjacent troughs. The frequency of respiration is calculated as the inverse of this time. We denote this feature "Time Domain Respiratory Frequency". All estimates of respiratory frequency were further normalized by subtracting (from each epoch's estimate of the frequency) the median value of that parameter over all epochs for the entire night. This was deemed a necessary step as the mean respiratory frequency will vary from subject to subject. The median was subtracted as it is more robust than the mean to outliers.

The complete list of features for each 30 s epoch is given in Table I, and we will use the indices from this table in referring to possible feature combinations.

Classifier Model Quadratic Discriminant Classifier

Following the feature extraction stage described above, each 30 s epoch now has an associated set of 27 features-9 RR-based, 6 EDR-based, 3 cross-spectral-based and 9 ribcage respiratory effort based. The classifier is a quadratic discriminant classifier (QDC), based on Bayes' rule. In deriving a decision rule for a QDC, gaussianity of the feature vector distributions, and independence between successive epochs is theoretically assumed. Neither gaussianity nor independence will necessarily be satisfied. In deriving the features above, we have attempted to ensure that each feature has an approximately Gaussian distribution. This can be ensured, for example, by using the logarithm of the spectral powers, rather than their absolute values. Classification accuracy may be improved if the dependence between epochs is considered as a post-processing step.

A quadratic discriminant classifier is derived as follows. Let $\omega_i$ signify the ith class. In this application there are three classes, S, W, and R. Let x denote the feature vector corresponding to a certain epoch. The feature vector in this case contains at most 27 elements, which are a selection of the features of Table I. Using Bayes' rule we wish to find the class i which will maximize the posterior probability:

$$P(\omega_i \mid x) = \frac{P(\omega_i) p(x \mid \omega_i)}{p(x)} \quad (1)$$

Maximizing the left hand side of (1) is equivalent to maximizing its logarithm. Therefore, assuming a normal distribution for the feature vector, $p(x|\omega_i)$ becomes:

$$p(x \mid \omega_i) = \frac{1}{(2\pi)^{d/2} |\Sigma_i|^{1/2}} \exp\left[-\frac{1}{2_0}(x - \mu_i)^T \Sigma_i^{-1} (x - \mu_i)\right] \quad (2)$$

where $\Sigma_i$ is the covariance matrix of the ith class, and $\mu_i$ is the mean vector of the ith class. Substituting (2) into the natural logarithm of (1), our problem is transformed into finding the class i which maximizes the discriminant value $g_{i(x)}$ for a given test feature vector x:

$$g_i(x) = x^T W_i x + w_i x + k_i \quad (3)$$

where:

$$W_i = -\frac{1}{2}\Sigma_i^{-1},$$

$$w_i = \Sigma_i^{-1} \mu_i$$

$$k_i = -\frac{1}{2}\mu_i^T \Sigma_i^{-1} \mu_i - \frac{1}{2} \ln|\Sigma_i| + \ln P(\omega_i)$$

The class with the highest discriminant value is chosen as the assigned class for that feature vector. To construct the quadratic discriminant classifier, therefore, we estimate the covariance matrix and mean for the features corresponding to each class, and also the prior probability of the class occurring.

It will be appreciated by one skilled in the art that a different classifier such as a linear discriminant classifier, a logistic discriminant classifier, a neural network, or a k-means clustering classifier could be used.

Feature Subset Selection

In theory, with quadratic or linear discriminant classifiers, the addition of features containing little or no relevant information in the classification process will not degrade the performance of the classifier. One could include all features in the classification process and features containing no information will be "ignored" by the classifier. In practice this is rarely true—null features add "noise" to the system, and the removal of these redundant features can greatly improve results. However, with 27 features to choose from, we are allowed $2^{27}$ feature subset combinations, so it not feasible to search all possible combinations. The classifier includes a process which allows efficient searching of the feature subset combinations.

A sequential forward floating search (SFFS) process identifies the feature subset that will optimize the classification performance. The k-coefficient is a measure of inter-rater agreement and takes into account the prior probability of a specific class occurring. The two raters under comparison are our sleep staging system and an expert polysomnograph annotator.

An SFFS algorithm operates as follows. Three passes are made with the ordinary sequential forward selection (SFS), so that three features are selected. One pass of the SFS simply adds the feature that most improves performance to the already selected features. Next, "unselection" of a selected feature is considered. The feature is found which most improves performance by its removal, and it is unselected. However, if no improvement is seen by the removal of any features then no features are unselected. Following the unselection phase the SFS is run again to select another feature. The cycle of a selection phase (with the SFS), followed by a possible unselection phase, is repeated until either the number of features required is reached, or until the SFS phase fails to select a feature immediately followed by the failure of the unselection phase to remove a feature, in which case it is impossible for the selected feature subset to change and the algorithm must terminate.

The advantage of the SFFS over the SFS, or other greedy feature selection algorithms, is its ability to avoid nesting. Nesting occurs in greedy selection algorithms if a feature is selected early on that is not a member of the optimal feature subset, as it cannot be removed. Another algorithm, the plus l, takeaway r algorithm, can also avoid nesting. Its operation is similar to the SFFS and it provides similar results but has a longer execution time as it always removes l features, whereas the SFFS judiciously decides whether to remove a feature or not. Indeed the SFFS may not find the optimal feature subset, as it is inherently a sub-optimal search, but will often yield results comparable with those of an exhaustive search.

The quadratic discriminant classifier model is used to discriminate between the three classes W, R, and S for a single subject's recording. To train the classifier (i.e., estimate class prior probabilities, covariance matrices, and means) 20% of the epochs for that night are randomly selected. Before the training data is chosen the prior probabilities for each of the three stages occurring are estimated using all 37 subjects. These probabilities are calculated as: P(W)=0.26, P(R)=0.13, P(S)=0.61. The training data is chosen in such a way that the ratios of each class are in the proportion of the prior probabilities where possible. However, if the covariance matrix of a class is estimated using as many (or less) observations than there are features, the matrix will be singular, prohibiting the use of discriminant analysis. In such cases the class containing insufficient observations is simply eliminated from the training data. To test the system the remaining 80% of the subject's epochs are presented to the classifier.

There are several means for assessing the performance of the system, including the overall accuracy (the percentage of correctly classified epochs from the test set), the absolute error from the true sleep efficiency, and Cohen's kappa statistic k. A k value above 0.7 is typically taken to indicate a high-degree of inter-system reliability. The accuracies and k obtained for each of the 37 subjects are averaged to give a mean accuracy and k. Each subject's accuracy and k. is itself derived from an ensemble of ten classifier runs, with differing selections of training data each time. The accuracies are derived from an ensemble average so as to remove any bias caused by the random selection of the training data.

Design of a Subject Independent Classifier

To construct a subject independent classifier, features from the other 36 subjects were pooled together to form the training data for the classifier, again training a 3-class—W, R, and S—classifier by estimating the class prior probabilities, covariance matrices, and means. This was repeated 37 times, leaving one subject out of the training data each time. In each case the remaining subject was used to test the system. Obtained accuracies and k from each of the 37 runs are averaged for an overall estimate of performance.

Design of an EEG Comparative Classifier

To gain a perspective on the results of the subject specific and subject independent systems, two further systems were designed using spectral and time domain features from the EEG in place of the cardiorespiratory features described. The EEG spectral features used are: average power in the delta (0.75-3.75 Hz), theta (4-7.75 Hz), alpha (8-12 Hz), spindle (12.25-15 Hz), and beta (15.25-30 Hz) frequency bands.

The powers in the designated frequency bands were calculated using a periodogram estimator. The 30-second EEG epoch was windowed using a sliding 2-second Hanning window with a 1-second overlap into 29 segments. The periodogram was constructed by averaging the square of the DFT of each segment over all 29 segments. The relevant frequency bands were then integrated to give the resulting band power.

The time domain features were the Hjorth parameters of activity, mobility and complexity. They were derived from the entire 30-second epoch. Letting x denote the EEG epoch containing N samples, the Hjorth parameters are defined as:

$$\text{Activity}(x) = \frac{1}{N}\sum_{i=1}^{N}(x_i - \mu_x)^2$$

$$\text{Mobility}(x) = \sqrt{\frac{\sigma(x')}{\sigma(x)}}$$

$$\text{Complexity}(x) = \frac{\text{Mobility}(x')}{\text{Mobility}(x)}$$

where x' is the first derivative of x, $\sigma(x)$ is the standard deviation of x, and $\mu_x$ is the mean of x. We also note that the activity is equal to the variance of x.

Using the same training and classifier paradigm as outlined above, the subject-specific and subject-independent classifiers were designed and tested.

Results

Subject Specific Results

Table II details the results for all subjects, and for subjects broken down by low and high AHI indices, after presenting all 27 features to the classifier.

TABLE II

SUBJECT SPECIFIC RESULTS

| Subject Group | Mean Cohen's Kappa Coefficient κ | Mean Accuracy | Average Sleep Efficiency Error |
|---|---|---|---|
| All | 0.56 ± 0.11 | 79% ± 5.4% | 3.3% |
| Low AHI | 0.6 ± 0.1 | 81% ± 4.6% | 2.5% |
| High AHI | 0.51 ± 0.09 | 77% ± 5.5% | 4% |

In Table III we list the features selected by the SFFS classifier. The indices listed refer to the feature list defined in Table I.

TABLE III

SUBJECT SPECIFIC FEATURES

| Subject group | Features Selected (in order of selection) |
|---|---|
| All | 9, 27, 21, 8, 18, 20, 2, 16 |
| Low AHI | 22, 9, 23, 8, 15, 19, 2, 16 |
| High AHI | 8, 2, 9, 23, 27, 20 |

Subject Independent Results

In Table IV we present the results for all subjects after presenting all 27 features to the classifier.

TABLE IV

SUBJECT INDEPENDENT RESULTS

| Subject Group | Mean Cohen's Kappa Coefficient κ | Mean Accuracy | Average Sleep Efficiency Error |
|---|---|---|---|
| All | 0.32 ± 0.11 | 67% ± 7.8% | 11% |
| Low AHI | 0.33 ± 0.1 | 68% ± 7.3% | 11.5% |
| High AHI | 0.31 ± 0.08 | 69% ± 7% | 10% |

Table V below lists the features selected by the features selection algorithm in the Subject Independent case.

TABLE V

SUBJECT INDEPENDENT FEATURES

| Subject group | Features Selected (in order of selection) |
|---|---|
| All | 22, 8, 20, 2, 4, 23, 5, 25, 9, 27, 21, 1, 11, 16, 17 |
| Low AHI | 19, 25, 4, 5, 8, 9, 16, 22, 12, 15, 11, 23 |
| High AHI | 8, 22, 2, 23, 25, 20, 14, 4, 16, 15 |

Low AHI Versus High AHI

We wish to investigate the difference in performance between subjects with low apnea-hypopnea indices (AHI) and those with high AHIs. We repeat the above-mentioned Subject Specific and Subject Independent experiments with the subjects split into low AHIs (<10 apneas or hypopneas per hour) and high AHIs. There were 14 subjects with high AHIs the mean AHI was 26 and the standard deviation was 19.8. The remaining 23 subjects with low AHIs had a mean AHI of 3.4 and a standard deviation of 2.2.

Comparative EEG Results

Tables VI and VII summarize the results of the Subject Specific and Subject Independent systems when trained using the 8 EEG features described earlier (no feature selection algorithm was used). As for the cardio-respiratory scoring system, we provide results broken down by high and low AHI class.

TABLE VI

EEG SUBJECT SPECIFIC RESULTS

| Subject Group | Mean Cohen's Kappa Coefficient κ | Mean Accuracy | Average Sleep Efficiency Error |
|---|---|---|---|
| All | 0.75 ± 0.12 | 87% ± 6.8% | 2.7% |
| Low AHI | 0.76 ± 0.12 | 87% ± 7.4% | 3% |
| High AHI | 0.73 ± 0.1 | 87% ± 5.8% | 2.2% |

TABLE VII

EEG SUBJECT INDEPENDENT RESULTS

| Subject Group | Mean Cohen's Kappa Coefficient κ | Mean Accuracy | Average Sleep Efficiency Error |
|---|---|---|---|
| All | 0.68 ± 0.15 | 84% ± 8% | 6.4% |
| Low AHI | 0.7 ± 0.16 | 84% ± 9.4% | 7.9% |
| High AHI | 0.68 ± 0.13 | 84% ± 7.7% | 5% |

There may be a delay inherent in some inductance plethysmograph devices. Although there was no delay associated with the device used in this study, some methods may contain a delay in recording, relative to the ECG, of 2 or 3 seconds. However, even when such a delay exists it is insignificant since we are using a 30 second epoch, and since only our interpretation of transitional epochs (epochs on the boundary of a sleep state change) will be affected by such a delay.

It will be appreciated that the invention provides for comprehensive analysis of sleep stages arising from the richness of the data incorporated in the features and the manner in which they are combined in the classifier. The classifier achieves effectively the same quality of output as a system which uses brain activity sensor inputs because it can be trained using such sensor inputs. Also, because of use of different threads, both cardiac and physical respiration (ribcage) threads, and cross-coupling of the features there is excellent robustness.

The invention is not limited to the embodiments described but may be varied in construction and detail. For example, a classifier other than that described above may be used.

The invention claimed is:

1. A sleep monitoring method performed by a system comprising a sensor interface and one or more processors, the method comprising the steps of:
    receiving, at the sensor interface, signals from a first sensor monitoring a cardiac activity of a patient;
    deriving, by the one or more processors, heart beat interval data from the signals received from the first sensor;
    extracting, by the one or more processors, one or more first time domain features and one or more first frequency domain features from the heart beat interval data;
    deriving, by the one or more processors, amplitude modulation data, caused by respiratory motion, from the signals received from the first sensor;
    extracting, by the one or more processors, one or more second time domain features and one or more second frequency domain features from the amplitude modulation data;
    combining, by the one or more processors operating as a classifier, one or more of the first extracted time domain features, one or more of the first extracted frequency domain features, one or more of the second extracted time domain features, and one or more of the second extracted frequency domain features;
    determining, by the one or more processors operating as the classifier, a plurality of sleep or wake stages of the patient based on the combined features, wherein the plurality of sleep or wake stages include one or more of (a) Wake stages, (b) Rapid Eye Movement (REM) Sleep stages, and (c) Non-REM Sleep stages; and
    generating, by the one or more processors, a plot indicating periods of the determined plurality of sleep or wake stages.

2. A computer program product comprising software code stored on non-transitory computer readable media which, when executed by a digital processor, performs the steps of the method of claim 1.

3. A sleep monitoring method as claimed in claim 1, wherein the determining is further based on probability distributions of the combined features.

4. A sleep monitoring method as claimed in claim 1, further comprising:
    extracting, by the one or more processors, one or more third frequency domain features from (a) one or more of the first extracted time domain features, (b) one or more of the first extracted frequency domain features, (c) one or more of the second extracted time domain features, or (d) one or more of the second extracted frequency domain features.

5. A sleep monitoring method as claimed in claim 4, wherein the one or more third frequency domain features includes (a) a power in a Very Low Frequency (VLF) band of a cross-spectrum of a series of RR intervals and a series of R-peak amplitudes, (b) a power in a Low Frequency (LF) band of a cross-spectrum of a series of RR intervals and a series of R-peak amplitudes, or (c) a power in a High Frequency (HF) band of a cross-spectrum of a series of RR intervals and a series of R-peak amplitudes.

6. A sleep monitoring method as claimed in claim 1, further comprising:
receiving, at the sensor interface, signals from a second sensor monitoring respiration of a patient;
deriving, by the one or more processors, direct respiration data from the signals received from the second sensor; and
extracting, by the one or more processors, one or more third time domain features and one or more third frequency domain features from the direct respiration data,
wherein the combining further comprises combining one or more of the third time domain features and one or more of the third frequency domain features.

7. A sleep monitoring method as claimed in claim 6, wherein the one or more third time domain features includes (a) an envelope power, (b) a breath-by-breath correlation, (c) a breath length variation, or (d) a time domain respiratory frequency.

8. A sleep monitoring method as claimed in claim 6, wherein the one or more third frequency domain features includes (a) a power in a Very Low Frequency (VLF) band of a ribcage respiratory effort signal, (b) a power in a Low Frequency (LF) band of a ribcage respiratory effort signal, or (c) a power in a High Frequency (HF) band of a ribcage respiratory effort signal.

9. A sleep monitoring method as claimed in claim 8, wherein (a) the VLF band ranges from 0.01 Hz to 0.05 Hz, (b) the LF band ranges from 0.05 Hz to 0.15 Hz, and (c) the HF band ranges from 0.15 Hz to 0.5 Hz.

10. A sleep monitoring method as claimed in claim 8, wherein the one or more third frequency domain features further includes (a) a third type of a mean respiratory frequency, which is defined by finding a frequency of maximum power in an HF band of a ribcage respiratory effort signal or (b) a power at a third type of a mean respiratory frequency.

11. A sleep monitoring method as claimed in claim 6, wherein the first sensor comprises an electrocardiogram (ECG) device and the second sensor comprises a plethysmogram device.

12. A sleep monitoring method as claimed in claim 1, wherein the one or more first time domain features includes (a) a mean of normalized RR intervals in an epoch, (b) a standard deviation of normalized RR intervals in an epoch, (c) a difference between a longest and a shortest normalized RR interval in an epoch, or (d) a mean of detrended RR intervals in an epoch.

13. A sleep monitoring method as claimed in claim 1, wherein the one or more second time domain features includes a standard deviation of R-peak amplitudes in an epoch.

14. A sleep monitoring method as claimed in claim 1, wherein the one or more first frequency domain features includes (a) a power in a Low Frequency (LF) band of a series of RR intervals, (b) a power in a High Frequency (HF) band of a series of RR intervals, or (c) an LF/HF power ratio.

15. A sleep monitoring method as claimed in claim 14, wherein (a) the LF band ranges from 0.05 Hz to 0.15 Hz and (b) the HF band ranges from 0.15 Hz to 0.5 Hz.

16. A sleep monitoring method as claimed in claim 14, wherein the one or more first frequency domain features further includes (a) a first type of a mean respiratory frequency, which is defined by finding a frequency of maximum power in an HF band of a series of RR intervals or (b) a power at a first type of a mean respiratory frequency.

17. A sleep monitoring method as claimed in claim 1, wherein the one or more second frequency domain features includes (a) a power in a Very Low Frequency (VLF) band of a series of R-peak amplitudes, (b) a power in a Low Frequency (LF) band of a series of R-peak amplitudes, or (c) a power in a High Frequency (HF) band of a series of R-peak amplitudes.

18. A sleep monitoring method as claimed in claim 17, wherein (a) the VLF band ranges from 0.01 Hz to 0.05 Hz, (b) the LF band ranges from 0.05 Hz to 0.15 Hz, and (c) the HF band ranges from 0.15 Hz to 0.5 Hz.

19. A sleep monitoring method as claimed in claim 17, wherein the one or more second frequency domain features further includes (a) a second type of a mean respiratory frequency, which is defined by finding a frequency of maximum power in an HF band of a series of R-peak amplitudes or (b) a power at a second type of a mean respiratory frequency.

20. A sleep monitoring method as claimed in claim 1, wherein the first sensor comprises an electrocardiogram (ECG) device.

* * * * *